US008488121B2

(12) United States Patent
Wang et al.

(10) Patent No.: US 8,488,121 B2
(45) Date of Patent: Jul. 16, 2013

(54) DEVICE FOR QUANTITATIVE ANALYSIS OF MICRO-VOLUME SOLUTION

(75) Inventors: Kuan-Hsiung Wang, Hsinchu (TW); Shuo-Ting Yan, Hsinchu (TW); Yueh-Chu Tien, Hsinchu (TW)

(73) Assignee: YAYATECH Corp. Ltd., Hsinchu (TW)

( * ) Notice: Subject to any disclaimer, the term of this patent is extended or adjusted under 35 U.S.C. 154(b) by 289 days.

(21) Appl. No.: 13/074,600

(22) Filed: Mar. 29, 2011

(65) Prior Publication Data
US 2012/0147374 A1 Jun. 14, 2012

(30) Foreign Application Priority Data

Dec. 13, 2010 (TW) .................................. 99143409 A (51) Int. Cl.
*G01N 21/17* (2006.01)
*C12P 19/34* (2006.01)
(52) U.S. Cl.
USPC ............. 356/436; 356/328; 435/91.2; 436/86
(58) Field of Classification Search
USPC ................. 356/432–440, 323, 325, 326, 328, 356/319; 435/6, 91.2, 303.1; 436/86, 6
See application file for complete search history.

(56) References Cited

U.S. PATENT DOCUMENTS

| 6,122,052 | A * | 9/2000 | Barnes et al. ................. 356/328 |
| 6,911,327 | B2 * | 6/2005 | McMillan et al. ............ 435/91.2 |
| 2005/0101025 | A1 * | 5/2005 | Ho .................................. 436/86 |
| 2009/0059225 | A1 * | 3/2009 | Robertson et al. ............ 356/326 |

* cited by examiner

*Primary Examiner* — Hoa Pham
(74) *Attorney, Agent, or Firm* — Muncy, Geissler, Olds & Lowe, PLLC (57) ABSTRACT

Provided herein is a device for quantitative analysis of a micro-volume solution. The device comprises a base portion provided with a light-emitting fiber, a movable arm provided with a light-receiving fiber, and at least one positioning block disposed between the movable arm and the base portion so that an optical path with a constant length is formed between the light-emitting fiber and the light-receiving fiber when the positioning block is clamped by the movable arm and the base portion. The solution concentration related to the absorbance with respect to the standard optical path length may be evaluated based on the built-in database and the optical intensity of light having passed through the solution as detected by a light sensor.

13 Claims, 9 Drawing Sheets

DEVICE FOR QUANTITATIVE ANALYSIS OF MICRO-VOLUME SOLUTION

1. FIELD OF THE INVENTION

The present invention generally relates to a device for quantitative analysis of a micro-volume solution and, more particularly, to a simple-structured and highly reliable device for quantitative analysis of a micro-volume solution.

2. BACKGROUND OF THE INVENTION

In biotechnological experiments, quantitative analysis of solutions containing biological samples (such as nucleic acids or proteins) is often required. Theoretically, the change of optical intensity (I) is adopted to calculate the optical density (O.D.) of the sample solution having a certain optical path length, i.e., the absorbance (A) of light at a specified wavelength that has passed through the sample solution having the optical path length, which may be expressed as:

$$O.D.=A=-Log(T)=-Log(I/I_0)$$

where A is the absorbance of light having passed through the sample solution, T is the transmittance, and I and $I_0$ denote the intensity of light having passed through the sample solution and a reference solution, respectively. Since the absorbance of light having passed through the solution in a quartz tube of 10-mm in width is conventionally used as a reference, the absorbance converted from the optical intensity as measured is normalized using the Beer-Lambert Law based on the 10-mm standard optical path to obtain the absorbance of light having passed through the sample solution having a 10-mm optical path.

According to the Beer-Lambert Law, the optical intensity of light having passed an absorbing medium by a certain depth weakens because part of the light has been absorbed by the absorbing medium. The optical intensity weakens as the concentration or the thickness of the absorbing medium increases. More particularly, the absorbance is proportional to the optical path length, which may be expresses as:

$$A_x/A_y=P_x/P_y$$

where A is the absorbance of light having passed through the sample solution, and $P_x$ and $P_y$ denote the lengths of optical paths x and y, respectively.

The dependence of the solution concentration (c) upon the optical path length P and the absorbance may be expressed as:

$$c=(A \times e)/P$$

where e is the wavelength-dependent extinction coefficient. For example, the e value is 50 ng-cm/μL for double-stranded deoxyribonucleic acids (DNA), 33 ng-cm/μL for single-stranded deoxyribonucleic acids, and 40 ng-cm/μL for ribonucleic nucleic acids (RNA). The nucleic acid concentration of the sample solution may be calculated according to the absorbance of the standard optical path length (10 mm) and the e value.

The proteins solution concentration may be calculated according to the Warburg-christian equation:

$$c=(1.55 \times A_{\lambda=280\ nm})-(0.76 \times A_{\lambda=260\ nm})$$

where c is the concentration (mg/ml), A is the absorbance, and λ is the wavelength.

Therefore, the concentration of the sample solution is conventionally calculated based on the relation with the absorbance, which is converted from the optical intensity of light having passed through the solution in a quartz tube. A spectrophotometer may be used for acquiring the transmittance spectrum in a wavelength range from 200 nm to 400 nm. To avoid light from being absorbed by the container during the ultra-violet wavelength range from 200 nm to 400 nm, a quartz tube may be used as the container.

However, such measurement requires a high-cost quartz tube and large volume of sample solution, but shows poor reproducibility and the sample solution cannot be recycledly used. Moreover, the difficulty in cleaning the quartz tube often causes contamination in the sample solution.

Figure 1:
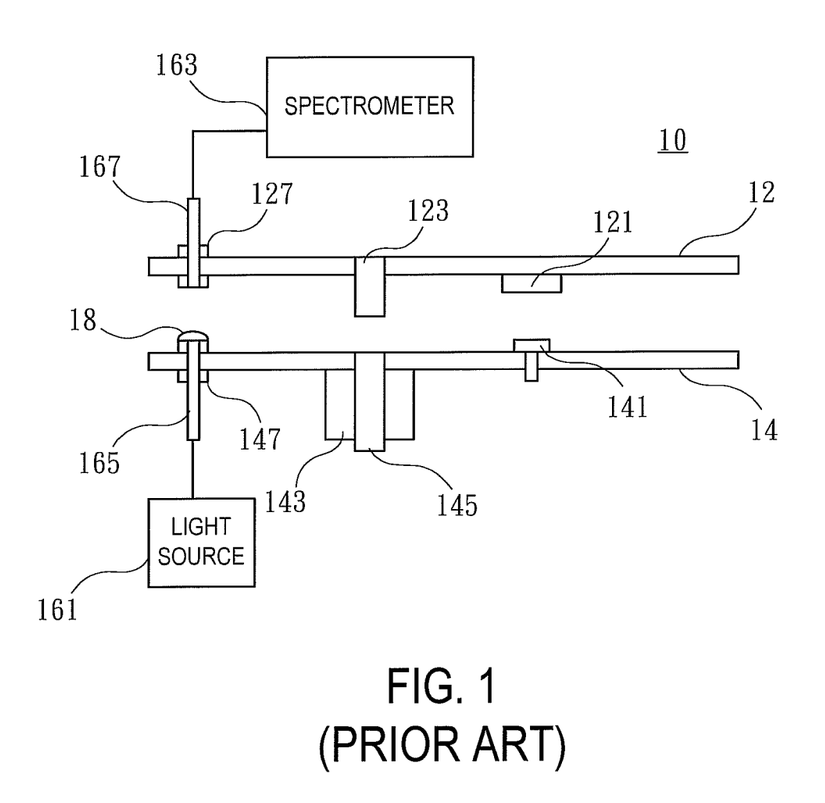
FIG. 1 is a cross-sectional diagram of a conventional device for quantitative analysis of nucleic acids.
Figure 2:
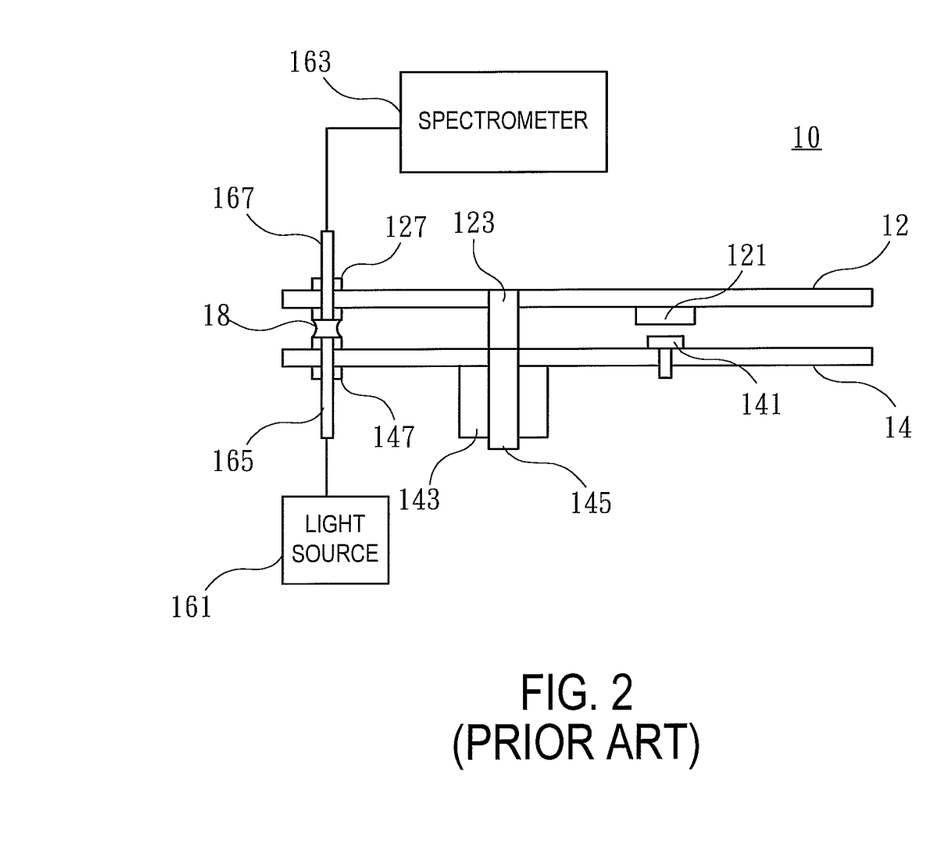
FIG. 2 is a cross-sectional diagram of a conventional device for quantitative analysis of nucleic acids of FIG. 1 at a second operation state.
Figure 3:
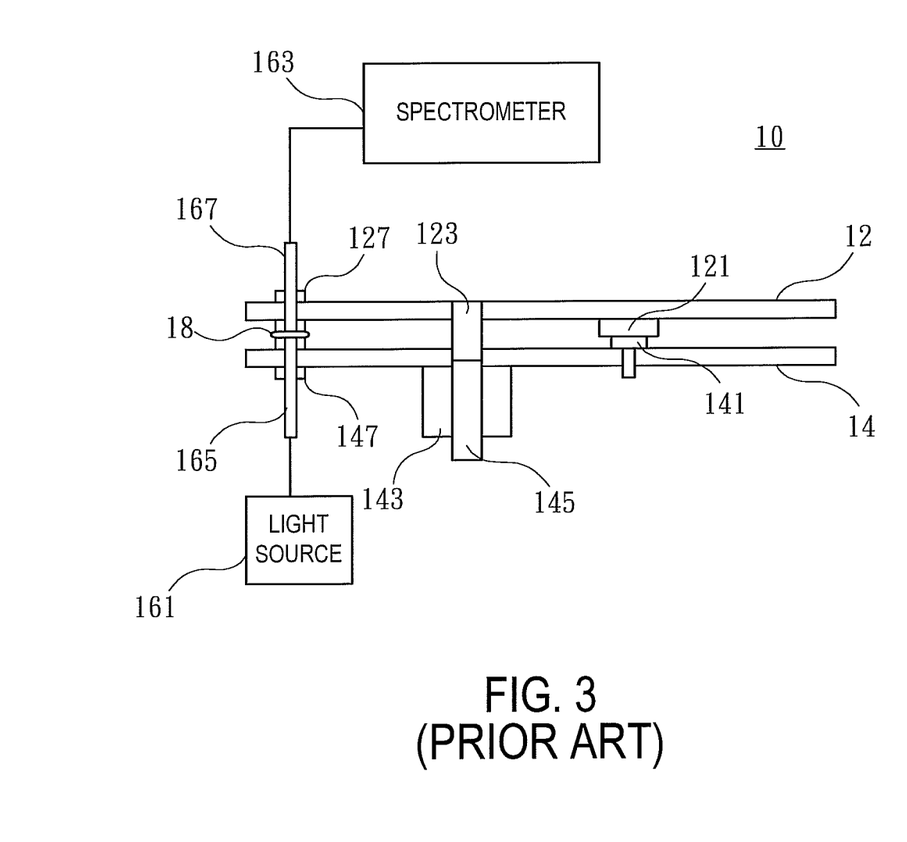
FIG. 3 is a cross-sectional diagram of a conventional device for quantitative analysis of nucleic acids of FIG. 1 at a third operation state.

Please refer to FIG. 1 to FIG. 3 for cross-sectional diagrams depicting various operation states of a conventional device for quantitative analysis of a nucleic acid solution. In these figures, an optical path is provided in the solution between two fibers due to the adhesion and surface tension of the solution.

The device 10 for quantitative analysis of a nucleic acid solution comprises a stationary arm 14 and a movable arm 12. The stationary arm 14 is provided with a bottom fiber base 147, a solenoid valve 143 and a screw head 141. The bottom fiber base 147 is used to fix a light-emitting fiber 165. The movable arm 12 comprises a magnet 121 disposed at the position corresponding to the screw head 141, a positioning screw 123 disposed at the position corresponding to the solenoid valve 143 and an upper fiber base 127 disposed at the position corresponding to the bottom fiber base 147 for fixing a light-receiving fiber 167.

At a first operation state as shown in FIG. 1, the movable arm 12 and the stationary atm 14 of the device 10 are separated. A nucleic acid solution 18 may be dripped on the bottom fiber base 147 and the light-emitting fiber 165 from a pipet.

Then the movable arm 12 moves downwards so that the positioning screw 123 contacts the plunger 145 in the solenoid valve 143 at a second operation state as shown in FIG. 2. Meanwhile, the upper fiber base 127 and the light-receiving fiber 167 also contact the nucleic acid solution 18. Due to the surface tension and the adhesion of the solution 18, the nucleic acid solution 18 is pulled by the bottom fiber base 147 and the upper fiber base 127 to form a first optical path between the light-emitting fiber 165 and the light-receiving fiber 167. The light emitted from the light source 161 travels through the light-emitting fiber 165 and the nucleic acid solution 18 to enter the light-receiving fiber 167, and is transmitted to the spectrometer 164 for spectrum-dividing and intensity measurement.

The plunger 145 moves downwards as the solenoid valve 143 is turned on. The movable arm 12 moves downwards due to the attractive force between the magnet 121 and the screw head 141 so that the magnet 121 contacts the screw head 141 at a third operation state as sown in FIG. 3. Meanwhile, a second optical path is formed between the light-emitting fiber 165 and the light-receiving fiber 167 even though the nucleic acid solution 18 is compressed.

After the optical intensity in the second optical path has been measured, the optical intensities for the first and the second optical paths are converted into the absorbances. Therefore, the nucleic acid concentration may be calculated according to the Beer-Lambert Law after the absorbance for the standard optical path is obtained by extrapolation.

However, such conventional device 10 for quantitative analysis of a nucleic acid solution comprises a complicated structure. The positioning screw 123 and the screw head 141 that are used for positioning at the second operation state and the third operation state may be loosened due to collision. This causes the variations of the first optical path length and the second optical path length and reduces the precision of the measurement. Accordingly, calibration is required after a certain usage count or a certain period of time, which leads to considerable time cost and maintenance cost.

Moreover, the device 10 for quantitative analysis of a nucleic acid solution is costly because a spectrometer 163 is used for spectrum-dividing and measurement.

SUMMARY OF THE INVENTION

It is one objective of the present invention to provide a device for quantitative analysis of a micro-volume solution with simple structure and high reliability.

It is another objective of the present invention to provide a device for quantitative analysis of a micro-volume solution, wherein only one optical path length is needed to calculate the solution concentration.

It is still another objective of the present invention to provide a device for quantitative analysis of a micro-volume solution, wherein the optical path length is kept constant by a positioning block.

It is still another objective of the present invention to provide a device for quantitative analysis of a micro-volume solution, wherein the positioning block and one of the movable arm, the base portion, or the combination thereof are formed as an unibody that improves the reliability of the device and the reproducibility of the measurement.

It is still another objective of the present invention to provide a device for quantitative analysis of a micro-volume solution with simple structure and low cost.

It is still another objective of the present invention to provide a device for quantitative analysis of a micro-volume solution, wherein a filter module is used to filter light with a wavelength for measurement to reduce the cost.

It is still another objective of the present invention to provide a device for quantitative analysis of a micro-volume solution, wherein the movable arm and the base portion comprise two light-emitting fibers and two light-receiving fibers, respectively, so as to form two optical paths with different lengths when the positioning block is clamped by the movable arm and the base portion.

It is still another objective of the present invention to provide a device for quantitative analysis of a micro-volume solution, wherein a groove is provided on the top surface of a base portion, and the groove has different widths at the upper portion and at the bottom portion so as to form optical paths with different lengths.

The present invention provides a device for quantitative analysis of a micro-volume solution, comprising: a base portion with a top surface, said base portion comprising a bottom fiber base for fixing a light-emitting fiber, said light-emitting fiber and said bottom fiber base forming a light-emitting surface for carrying a solution droplet; a movable arm with a bottom surface disposed above said base portion, said movable arm being capable of moving upwards and downwards and comprising an upper fiber base disposed at the position corresponding to said bottom fiber base for fixing a light-receiving fiber, said light-receiving fiber and said upper fiber base forming a light-receiving surface; at least one positioning block disposed selectively on said bottom surface of said movable arm, on said top surface of said base portion, between said movable arm and said base portion or the combination thereof; a light source for generating a light beam being coupled to said light-emitting fiber so that said light beam is transmitted to said light-receiving fiber from said light-emitting surface; a filter module connected to said light-receiving fiber, said filter module being capable of allowing light with a required wavelength to pass through and being coupled to a photo detecting module and a database in order; wherein said solution droplet forms an optical path with a constant length between said light-emitting surface and said light-receiving surface due to surface tension and adhesion when said movable arm moves downwards and clamps said positioning block between said movable arm and said base portion.

The present invention further provides a device for quantitative analysis of a micro-volume solution, comprising: a base portion with a top surface, said base portion comprising a first bottom fiber base and a second bottom fiber base for fixing a first light-emitting fiber and a second light-emitting fiber, respectively, said first light-emitting fiber, said second light-emitting fiber, said first bottom fiber base and said second bottom fiber base forming a light-emitting surface for carrying a solution droplet; a movable arm with a bottom surface disposed above said base portion, said movable arm being capable of moving upwards and downwards and comprising a first upper fiber base and a second upper fiber base disposed at the position corresponding to said first bottom fiber base and said second bottom fiber base for fixing a first light-receiving fiber and a second light-receiving fiber, said first light-receiving fiber and said first upper fiber base forming a first light-receiving surface, said second light-receiving fiber and said second upper fiber base forming a second light-receiving surface, and an altitude difference appearing between said first light-receiving surface and said second light-receiving surface; at least one positioning block disposed selectively on said bottom surface of said movable arm, on said top surface of said base portion, between said movable arm and said base portion or the combination thereof; a light source for generating two light beams being coupled to said first light-emitting fiber and said second light-emitting fiber so that said light beams are transmitted to said first light-receiving fiber and said second light-receiving fiber from said light-emitting surface; a filter module connected to said first light-receiving fiber and said second light-receiving fiber, said filter module being capable of allowing light with a required wavelength to pass through; and a photo detecting module coupled to said filter module so as to receive and detect the optical intensity of light of said wavelength; wherein said solution droplet forms a first optical path and a second optical path between said light-emitting surface and said first light-receiving surface and between said light-emitting surface and said second light-receiving surface due to surface tension and adhesion when said movable arm moves downwards and clamps said positioning block between said movable arm and said base portion.

The present invention further provides a device for quantitative analysis of a micro-volume solution, comprising: a base portion comprising a groove on a top surface, said groove comprising a bottom portion with a first width and an upper portion with a second width so that said groove is capable of carrying a solution droplet; a first light-emitting fiber disposed on one side of said bottom portion of said groove; a second light-emitting fiber disposed on one side of said upper portion of said groove, said second light-emitting fiber and said first light-emitting fiber being disposed on the same side; a first light-receiving fiber disposed on one side of said bottom portion of said groove, said first light-receiving fiber being disposed opposite to said first light-emitting fiber; a second light-receiving fiber disposed on one side of said upper portion of said groove, said second light-receiving fiber being disposed opposite to said second light-emitting fiber; a light source for generating two light beams being coupled to said first light-emitting fiber and said second light-emitting fiber so that said light beams are transmitted to said first light-receiving fiber and said second light-receiving fiber from said solution droplet; a filter module connected to said first light-receiving fiber and said second light-receiving fiber, said filter module being capable of allowing light with a required wavelength to pass through; and a photo detecting module coupled to said filter module so as to receive and detect the optical intensity of light of said wavelength.

BRIEF DESCRIPTION OF THE DRAWINGS

The objectives and spirits of the embodiments of the present invention will be readily understood by the accompanying drawings and detailed descriptions.

DETAILED DESCRIPTION OF THE PREFERRED EMBODIMENTS

The present invention can be exemplified but not limited by various embodiments as described hereinafter.

Figure 4:
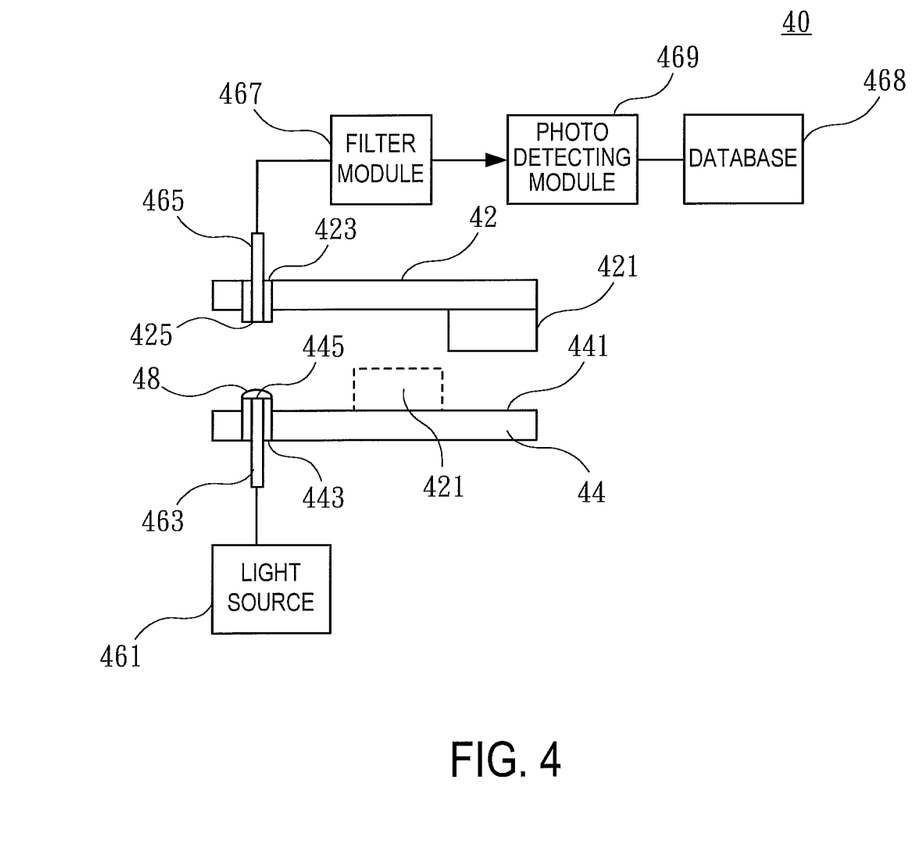
FIG. 4 is a cross-sectional diagram of a device for quantitative analysis of a micro-volume solution in accordance with one embodiment of the present invention.
Figure 5:
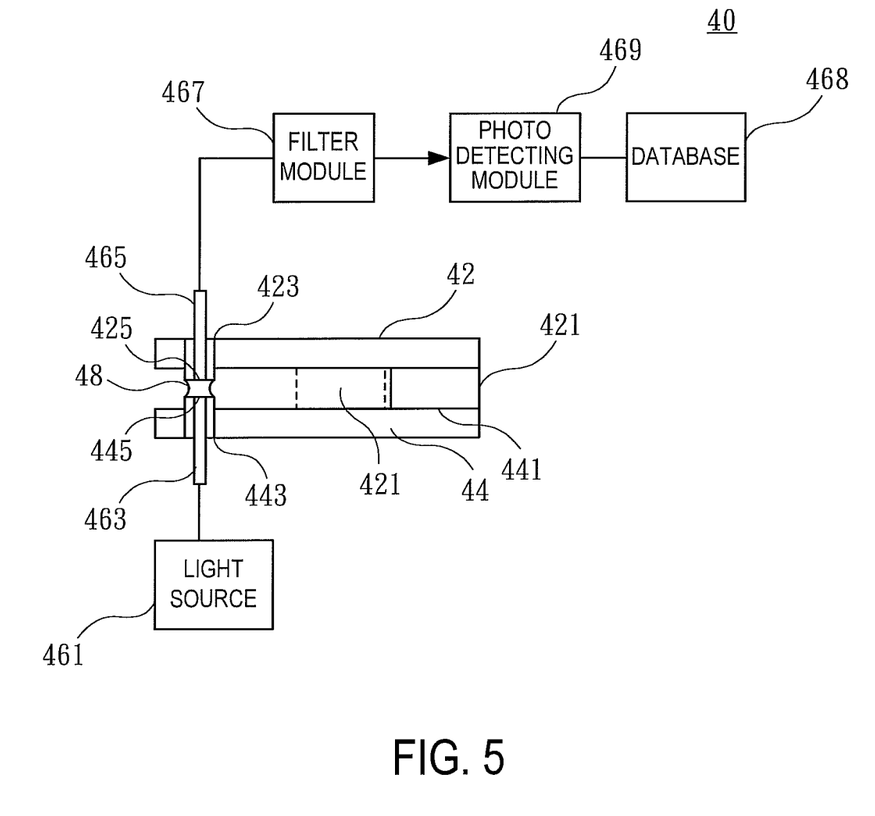
FIG. 5 is a cross-sectional diagram of a device for quantitative analysis of a micro-volume solution of FIG. 4 at a second operation state.

Please refer to FIG. 4 and FIG. 5 for cross-sectional diagrams of a device for quantitative analysis of a micro-volume solution at different operation states, respectively, in accordance with one embodiment of the present invention. In the present invention, the device 40 for quantitative analysis of a micro-volume solution comprises a base portion 44, a movable arm 42, at least one positioning block 421, a light source 461, a filter module 467, a photo detecting module 469 and a database 468.

The base portion 44 comprises a bottom fiber base 443 for fixing a light-emitting fiber 463. The light-emitting fiber 463 and the bottom fiber base 443 form a light-emitting surface 445 for carrying a solution droplet 48. The movable arm 42 comprises an upper fiber base 423 disposed at the position corresponding to the bottom fiber base 443 for fixing a light-receiving fiber 465. The light-receiving fiber 465 and the upper fiber base 423 form a light-receiving surface 425. The positioning block 421 may be disposed selectively on the bottom surface of the movable arm 42, on the top surface of the base portion 44, between the movable arm 42 and the base portion 44, or the combination thereof.

The solution droplet 48 forms an optical path with a constant length between the light-emitting surface 445 and the light-receiving surface 425 due to surface tension and adhesion when the movable arm 42 moves downwards to clamp the positioning block 421 between the movable arm 42 and the base portion 44, as shown in FIG. 5.

The light source 461 is capable of generating a light beam coupled to the light-emitting fiber 463. The light beam is transmitted to the filter module 467 from the light-receiving fiber 465 after it has traveled through the optical path formed by the solution droplet 48 between the light-emitting surface 445 and the light-receiving surface 425. The filter module 467 is connected to the light-receiving fiber 465 and is capable of allowing light with required wavelength to pass through and be detected by a photo detecting module 469.

The detected optical intensity data is then converted into the absorbance according to the optical path length. The data according to another optical path is stored in a database 468 and may be used to calculate the absorbance according to the standard optical path with a length of 10 mm to calculate the solution concentration.

The positioning block 421 disposed on the bottom surface of the movable arm 42 and the movable arm 42 are formed as a unibody. Moreover, if the base portion 44 is also provided with a positioning block 421 disposed on the top surface 441, the positioning block 421 and the base portion 44 are preferably formed as a unibody. In this manner, the device has simple structure and high reliability without additional calibration required.

The light beam from the light source 461 comprises ultraviolet light with a wavelength range from 200 nm to 400 nm. The filter module 467 may comprise a 230-nm filter, a 260-nm filter and a 280-nm filter capable of allowing light with a wavelength of 230 nm, 260 nm and 280 nm to pass through, respectively. The photo detecting module 469 comprises at least one photo detector, for example, a photodiode, for detecting the optical intensity of light having passed through the filter module 467. The data according to another optical path is stored in the database 468 and may be used to calculate the absorbance according to the standard optical path.

Figure 6:
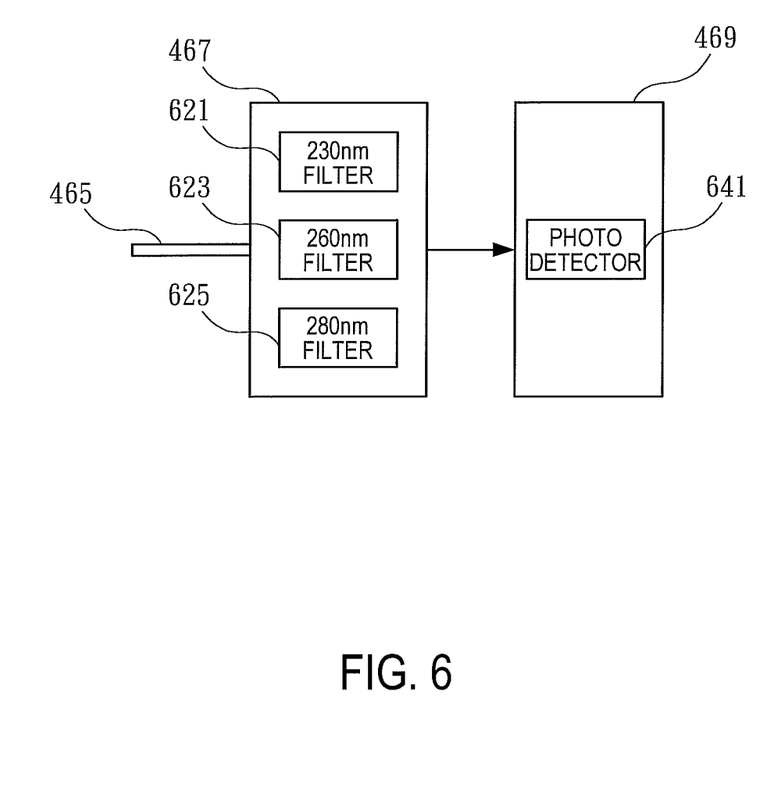
FIG. 6 is a schematic diagram of a filter module and a photo detecting module in accordance with one preferred embodiment of the present invention.

Please refer to FIG. 6, which is a schematic diagram of a filter module and a photo detecting module in accordance with one embodiment of the present invention. The filter module 467 of the present invention may comprise a 230-nm filter 621, a 260-nm filter 623 and a 280-nm filter 625 and is capable of switching to one of the 230-nm filter 621, the 260-nm filter 623 and the 280-nm filter 625 so as to allow light with a wavelength of 230 nm, 260 nm and 280 nm to pass through, respectively. The photo detecting module 469 comprises a photo detector 641 for measuring the optical intensity of light with a wavelength of 230 mm, 260 mm and 280 nm in turn.

Figure 7:
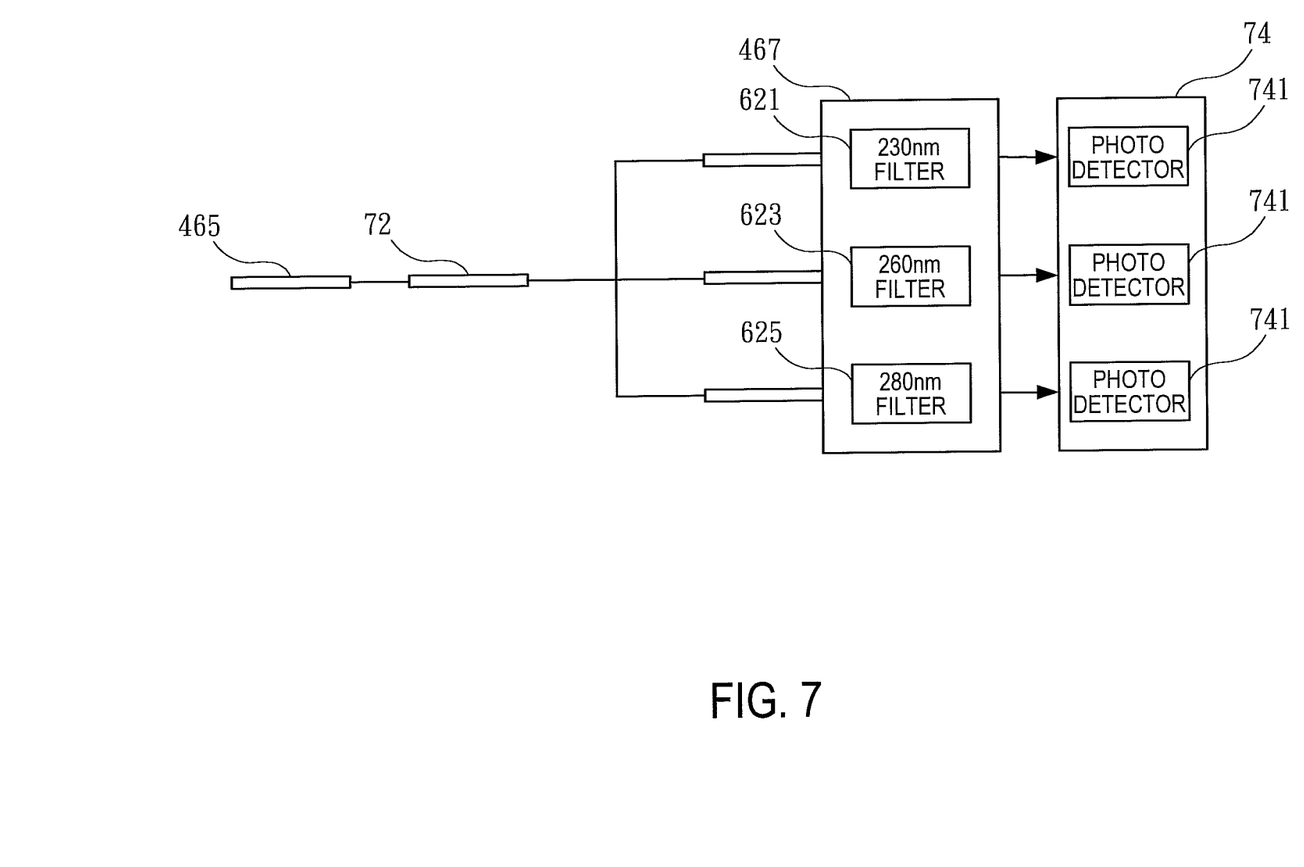
FIG. 7 is a schematic diagram of a filter module and a photo detecting module in accordance with another embodiment of the present invention.

Please refer to FIG. 7, which is a schematic diagram of a filter module and a photo detecting module in accordance with another embodiment of the present invention. In FIG. 7, the filter module 467 of the present embodiment comprises a 230-nm filter 621, a 260-nm filter 623 and a 280-nm filter 625 capable of allowing light with a wavelength of 230 nm, 260 nm and 280 nm to pass through, respectively. The photo detecting module 74 comprises three photo detectors 741 corresponding to the three filters 621, 623, 625 for measuring the optical intensity of light with a wavelength of 230 nm, 260 nm and 280 nm respectively.

In the present embodiment, a one-to-three fiber 72 is further provided between the filter module 467 and the light-receiving fiber 465. The diameter of the light-receiving fiber 465 is larger than that of the light-emitting fiber 463 so that light having passed through the solution droplet 48 is completely received. The diameter at one end of the one-to-three fiber 72 is smaller than the light-receiving fiber 465 so as to split the light beam into three secondary light beams. In this manner, the secondary light beams are transmitted to the filter 621, 623 and 625 of the filter module 467, respectively. The filtered light beams with a wavelength of 230 nm, 260 nm and 280 nm, respectively, are then detected by the corresponding photo detectors 741 of the photo detecting module 74 to obtain the optical intensity. The concentration as well as the measurement reliability can be obtained.

Figure 8:
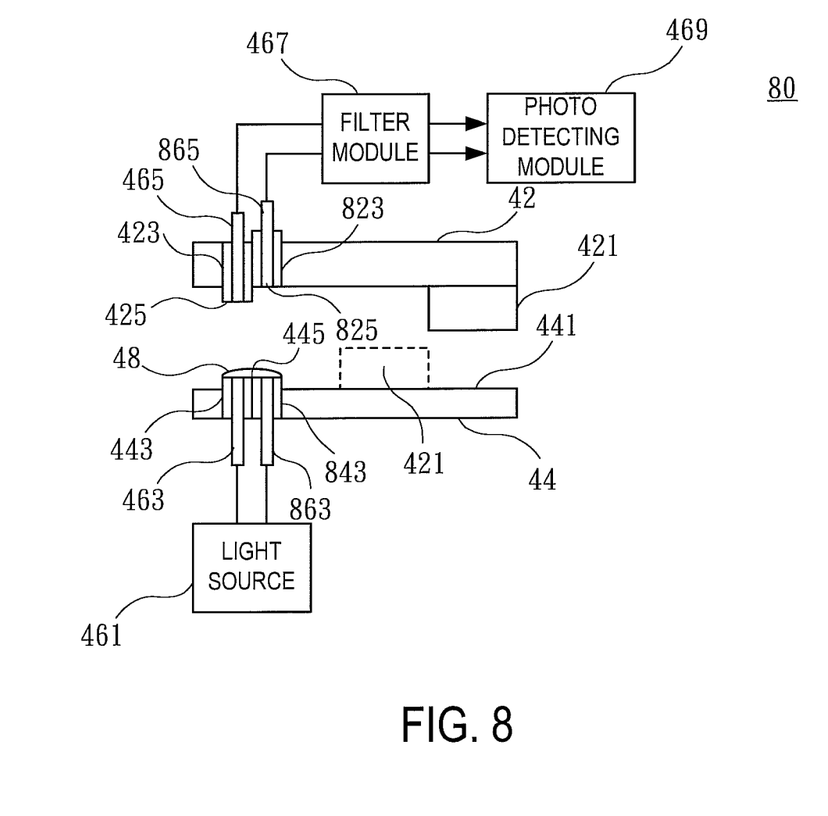
FIG. 8 is a cross-sectional diagram of a device for quantitative analysis of a micro-volume solution in accordance with another embodiment of the present invention.

Please refer to FIG. 8, which is a cross-sectional diagram of a device for quantitative analysis of a micro-volume solution in accordance with another embodiment of the present invention. In FIG. 8, the device 80 for quantitative analysis of a micro-volume solution of the present embodiment is similar to the device 40 of the embodiment in FIG. 4. The device 80 comprises a base portion 44, a movable arm 42, at least one positioning block 421, a light source 461, a filter module 467 and a photo detecting module 469.

More particularly, the base portion 44 comprises a bottom fiber base 443 (also referred to as a first bottom fiber base) and a second bottom fiber base 843 for fixing a light-emitting fiber 463 (also referred to as a first light-emitting fiber) and a second light-emitting fiber 863. The light-emitting fiber 463, the second light-emitting fiber 863, the bottom fiber base 443 and the second bottom fiber base 843 form a light-emitting surface 445 for carrying a solution droplet 48. The movable arm 42 is provided with an upper fiber base 423 (also referred to as a first upper fiber base) and a second upper fiber base 823 disposed at the position corresponding to the bottom fiber base 443 and the second bottom fiber base 843 for fixing a light-receiving fiber 465 (also referred to as a first light-receiving fiber) and a second light-receiving fiber 865. The light-receiving fiber 465 and the upper fiber base 423 form a light-receiving surface 425. The second light-receiving fiber 865 and the second upper fiber base 823 form a second light-receiving surface 825.

The solution droplet 48 adheres to the light-receiving surface 425 and the second light-receiving surface 825 and thus forms two optical paths with constant lengths between the light-emitting surface 445 and the light-receiving surface 425 and between the light-emitting surface 445 and the second light-receiving surface 825 due to surface tension and adhesion when the movable arm 42 moves downwards and clamps the positioning block 421 between the movable arm 42 and the base portion 44. Since the light-receiving surface 425 and the second light-receiving surface 825 of the present embodiment have different altitudes, two different optical path lengths can be obtained.

The light source 461 is capable of generating two light beams coupled respectively to the light-emitting fiber 463 and the second light-emitting fiber 863. The light beams are transmitted to the filter module 467 and the photo detecting module 469 from the light-receiving fiber 465 and the second light-receiving fiber 865 after they have traveled respectively through the optical paths formed by the solution droplet 48 between the light-emitting surface 445 and the light-receiving surface 425 and between the light-emitting surface 445 and the second light-receiving surface 825. The filter module 467 is connected to the light-receiving fiber 465 and the second light-receiving fiber 865 and is capable of allowing light of required wavelengths to pass through and be detected by the photo detecting module 469.

The detected optical intensity data is then converted into the absorbances according to the two optical path lengths. Then the absorbance according to the standard optical path with a length of 10 mm is obtained to calculate the solution concentration.

In another embodiment of the present invention, the light-receiving fiber 465 and the second light-receiving fiber 865 may be respectively provided with a one-to-three fiber 72 of FIG. 7, for example, a first one-to-three fiber and a second one-to-three fiber. The first one-to-three fiber is coupled to the first light-receiving fiber 465 at one end, and the second one-to-three fiber is coupled to the second light-receiving fiber 865 at one end. The received light beams are splitted into three secondary light beams respectively, which are then filtered by the 230-nm filter, the 260-nm filter and the 280-nm filter of the filter module 467 and detected by the photo detecting module 469 to obtain the optical intensity of light according to each wavelength.

Figure 9:
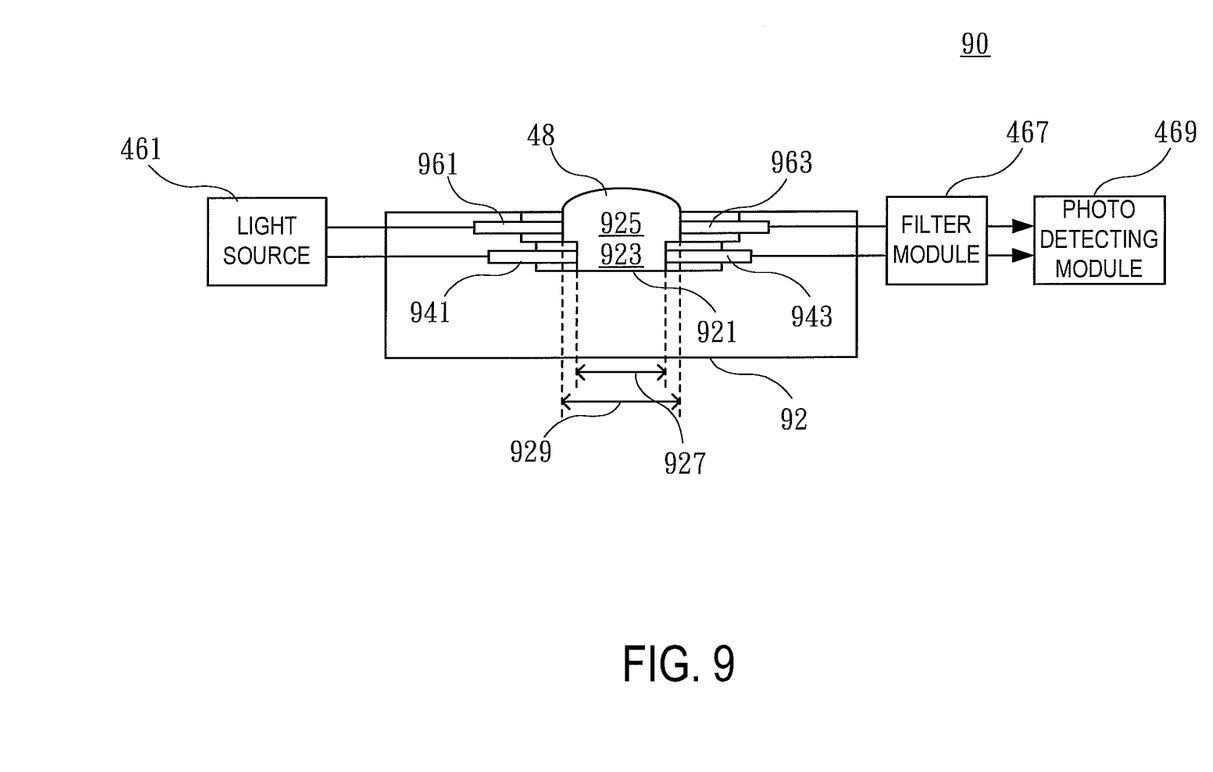
FIG. 9 is a cross-sectional diagram of a device for quantitative analysis of a micro-volume solution in accordance with another embodiment of the present invention.

Please refer to FIG. 9, which is a cross-sectional diagram of a device for quantitative analysis of a micro-volume solution in accordance with another embodiment of the present invention. In the present embodiment, the device 90 for quantitative analysis of a micro-volume solution adopts a light source 461, a filter module 467 and a photo detecting module 469, which are similar to those as aforementioned. The base portion 92 of the present embodiment comprises a groove 921 on the top surface. The groove 921 comprises a bottom portion 923 and an upper portion 925. More particularly, the bottom portion 923 has a first width 927, and the upper portion 925 has a second width 929.

The first light-emitting fiber 941 is disposed on one side of the bottom portion 923, and the first light-receiving fiber 943 is disposed on another side of the bottom portion 923 opposite to the first light-emitting fiber 941. The second light-emitting fiber 961 is disposed on one side of the upper portion 925. The second light-emitting fiber 961 and the first light-emitting fiber 941 are disposed on the same side. The second light-receiving fiber 963 is disposed on one side of the upper portion 925 opposite to the second light-emitting fiber 961. The solution droplet 48 is disposed in the groove 921 to fill the bottom portion 923 and the upper portion 925.

The light source 461 is capable of generating two light beams coupled respectively to the first light-emitting fiber 941 and the second light-emitting fiber 961. The light beams are transmitted to the filter module 467 and the photo detecting module 469 from the first light-receiving fiber 943 and the second light-receiving fiber 963 after they have traveled through the optical path with a first width 927 and the optical path with a second width 929 formed by the solution droplet 48 in the bottom portion 923 and the upper portion 925 of the groove 921. The filter module 467 is connected to the first light-receiving fiber 943 and the second light-receiving fiber 963 and is capable of allowing light of required wavelengths to pass through and be detected by the photo detecting module 469.

The detected optical intensity data is then converted into the absorbances according to the two optical path lengths. Then the absorbance according to the standard optical path with a length of 10 mm is obtained to calculate the solution concentration.

Similarly, in another embodiment, the first light-receiving fiber 943 and the second light-receiving fiber 963 may be respectively provided with a one-to-three fiber 72 of FIG. 7, for example, a first one-to-three fiber and a second one-to-three fiber. The first one-to-three fiber is coupled to the first light-receiving fiber 943 at one end, and the second one-to-three fiber is coupled to the second light-receiving fiber 963 at one end. The received light beams are splitted into three secondary light beams respectively, which are then filtered by the 230-nm filter, the 260-nm filter and the 280-nm filter of the filter module 467 and detected by the photo detecting module 469 to obtain the optical intensity of light according to each wavelength.

In the aforementioned embodiments, each of the light-emitting fiber of the devices 40 and 80 for quantitative analysis of a micro-volume solution can also be disposed in the movable arm, and each of the light-receiving fiber is disposed in the base portion accordingly. Furthermore, the movable arm 42 can be disposed under the base portion 44, and the at least one positioning block 421 is disposed between the movable arm 42 and the base portion 44.

In the aforementioned embodiments, the devices 40, 80, 90 for quantitative analysis of a micro-volume solution require only a 2-μL solution droplet for concentration measurement. The device of the present invention has simple structure, and yields high reliability and high reproducibility. Moreover, the components in the device will not be loosened or deformed due to collision, and thus no periodical calibration is required. Therefore, the present invention is advantageous in low manufacture cost and time cost.

Although this invention has been disclosed and illustrated with reference to particular embodiments, the principles involved are susceptible for use in numerous other embodiments that will be apparent to persons skilled in the art. This invention is, therefore, to be limited only as indicated by the scope of the appended claims.

What is claimed is:

1. A device for quantitative analysis of a micro-volume solution, comprising:
    a base portion with a top surface, said base portion comprising a bottom fiber base for fixing a light-emitting fiber, said light-emitting fiber and said bottom fiber base forming a light-emitting surface for carrying a solution droplet;
    a movable arm with a bottom surface disposed above said base portion, said movable arm being capable of moving upwards and downwards and comprising an upper fiber base disposed at the position corresponding to said bottom fiber base for fixing a light-receiving fiber, said light-receiving fiber and said upper fiber base forming a light-receiving surface;
    at least one positioning block disposed selectively on said bottom surface of said movable arm, on said top surface of said base portion, between said movable arm and said base portion or the combination thereof;
    a light source for generating a light beam being coupled to said light-emitting fiber so that said light beam is transmitted to said light-receiving fiber from said light-emitting surface; and
    a filter module connected to said light-receiving fiber and coupled to a photo detecting module and a database in order, said filter module being capable of allowing light with the required wavelength to pass through;
    wherein said solution droplet forms an optical path with a constant length between said light-emitting surface and said light-receiving surface due to surface tension and adhesion when said movable arm moves downwards and clamps said positioning block between said movable arm and said base portion.

2. The device for quantitative analysis of a micro-volume solution as recited in claim 1, wherein said at least one positioning block and one of said movable arm, said base portion or the combination thereof are formed as a unibody.

3. The device for quantitative analysis of a micro-volume solution as recited in claim 1, wherein said filter module comprises a 230-nm filter, a 260-nm filter and a 280-nm filter capable of allowing light with a wavelength of 230 nm, 260 nm and 280 nm to pass through, respectively.

4. The device for quantitative analysis of a micro-volume solution as recited in claim 3, wherein said filter module is capable of switching to one of said 230-nm filter, said 260-nm filter or said 280-nm filter so as to allow light with a wavelength of 230 nm, 260 nm and 280 nm to pass through, respectively, and to be measured by said photo detecting module in turn.

5. The device for quantitative analysis of a micro-volume solution as recited in claim 3, further comprising a one-to-three fiber with one end coupled to said light-receiving fiber to split said light beam into three secondary light beams to be filtered by said 230-nm filter, said 260-nm filter and said 280-nm filter, respectively, and to be measured by said photo detecting module.

6. The device for quantitative analysis of a micro-volume solution as recited in claim 1, wherein said light-emitting fiber can be disposed in said movable arm, and said light-receiving fiber is disposed in said base portion accordingly.

7. The device for quantitative analysis of a micro-volume solution as recited in claim 1, wherein said movable arm can be disposed under said base portion.

8. A device for quantitative analysis of a micro-volume solution, comprising:
    a base portion with a top surface, said base portion comprising a first bottom fiber base and a second bottom fiber base for fixing a first light-emitting fiber and a second light-emitting fiber, respectively, said first light-emitting fiber, said second light-emitting fiber, said first bottom fiber base and said second bottom fiber base forming a light-emitting surface for carrying a solution droplet;
    a movable arm with a bottom surface disposed above said base portion, said movable arm being capable of moving upwards and downwards and comprising a first upper fiber base and a second upper fiber base disposed at the position corresponding to said first bottom fiber base and said second bottom fiber base for fixing a first light-receiving fiber and a second light-receiving fiber, said first light-receiving fiber and said first upper fiber base forming a first light-receiving surface, said second light-receiving fiber and said second upper fiber base forming a second light-receiving surface, and an altitude difference appearing between said first light-receiving surface and said second light-receiving surface;
    at least one positioning block disposed selectively on said bottom surface of said movable arm, on said top surface of said base portion, between said movable arm and said base portion or the combination thereof;
    a light source for generating two light beams being coupled to said first light-emitting fiber and said second light-emitting fiber so that said light beams are transmitted to said first light-receiving fiber and said second light-receiving fiber from said light-emitting surface;
    a filter module connected to said first light-receiving fiber and said second light-receiving fiber, said filter module being capable of allowing light with the required wavelength to pass through; and
    a photo detecting module coupled to said filter module so as to receive and detect the optical intensity of light of the required wavelength;
    wherein said solution droplet forms a first optical path and a second optical path between said light-emitting surface and said first light-receiving surface and between said light-emitting surface and said second light-receiving surface due to surface tension and adhesion when said movable arm moves downwards and clamps said positioning block between said movable arm and said base portion.

9. The device for quantitative analysis of a micro-volume solution as recited in claim 8, wherein said at least one positioning block and one of said movable arm, said base portion or the combination thereof are formed as a unibody.

10. The device for quantitative analysis of a micro-volume solution as recited in claim 8, wherein said filter module comprises a 230-nm filter, a 260-nm filter and a 280-nm filter capable of allowing light with a wavelength of 230 nm, 260 nm and 280 nm to pass through, respectively.

11. The device for quantitative analysis of a micro-volume solution as recited in claim 10, wherein said filter module is capable of switching to one of said 230-nm filter, said 260-nm filter or said 280-nm filter so as to allow light with a wavelength of 230 nm, 260 nm and 280 nm to pass through, respectively, and to be measured by said photo detecting module in turn.

12. The device for quantitative analysis of a micro-volume solution as recited in claim 10, further comprising a first one-to-three fiber and a second one-to-three fiber with one end coupled to said first light-receiving fiber and said second light-receiving fiber, respectively, to split said light beams into three secondary light beams to be filtered by said 230-nm filter, said 260-nm filter and said 280-nm filter, respectively, and to be measured by said photo detecting module.

13. The device for quantitative analysis of a micro-volume solution as recited in claim 8, wherein said first light-emitting fiber and said second light-emitting fiber can be disposed in said movable arm, and said first light-receiving fiber and said second light-receiving fiber are disposed in said base portion accordingly.

* * * * *